US009145578B2

(12) United States Patent
Itoh et al.

(10) Patent No.: US 9,145,578 B2
(45) Date of Patent: Sep. 29, 2015

(54) METHOD FOR ASSAYING CHOLESTEROL IN APOE-CONTAINING HDL

(75) Inventors: Yasuki Itoh, Niigata (JP); Hitoshi Chiba, Hokkaido (JP)

(73) Assignees: Denka Seiken Co., Ltd., Tokyo (JP); National University Corporation Hokkaido University, Hokkaido (JP)

( * ) Notice: Subject to any disclaimer, the term of this patent is extended or adjusted under 35 U.S.C. 154(b) by 0 days.

(21) Appl. No.: 13/503,924

(22) PCT Filed: Oct. 26, 2010

(86) PCT No.: PCT/JP2010/068883
§ 371 (c)(1),
(2), (4) Date: Apr. 25, 2012

(87) PCT Pub. No.: WO2011/052550
PCT Pub. Date: May 5, 2011

(65) Prior Publication Data
US 2012/0208219 A1 Aug. 16, 2012

(30) Foreign Application Priority Data
Oct. 26, 2009 (JP) ................................. 2009-245476

(51) Int. Cl.
*C12Q 1/60* (2006.01)
(52) U.S. Cl.
CPC ....................................... *C12Q 1/60* (2013.01)
(58) Field of Classification Search
None
See application file for complete search history.

(56) References Cited

U.S. PATENT DOCUMENTS 4,892,815 A    1/1990  Kerscher et al.
2009/0181413 A1*  7/2009  Itoh et al. .................. 435/11

FOREIGN PATENT DOCUMENTS

EP    1 342 792 A1    9/2003
EP    1 555 326 A1    7/2005
JP    2001-346598    * 12/2001

OTHER PUBLICATIONS 9016-45-9 synonyms, accessed from the ACS, Apr. 1, 2013.*
pdf entitled "CAS No. 9002-92-0" downloaded from http://www.commonchemistry.org/ChemicalDetail.aspx?ref=9002-92-0 on Jan. 16, 2014.*
JP 2001-346598 JPO English translation.*

(Continued)

*Primary Examiner* — Ralph Gitomer
*Assistant Examiner* — Trent Clarke
(74) *Attorney, Agent, or Firm* — Foley & Lardner LLP

(57) ABSTRACT

This invention provides a method for separately or simultaneously quantifying cholesterol in a total amount of HDL-C, cholesterol in an HDL subfraction of apoE-containing HDL-C, and cholesterol in an HDL subfraction of apoE-deficient HDL-C. The method comprises enzymatically and separately quantifying cholesterol in apoE-containing HDL and cholesterol in apoE-deficient HDL by adding a surfactant selected from the group consisting of a surfactant with an apoE-containing HDL response rate/apoE-deficient HDL response rate ratio of 0.7 to less than 1.3, a surfactant with an apoE-containing HDL response rate/apoE-deficient HDL response rate ratio of less than 0.7, and a surfactant with an apoE-containing HDL response rate/apoE-deficient HDL response rate ratio of 1.3 or more to a test sample, allowing cholesterol esterase and cholesterol oxidase to react therewith, and quantifying the hydrogen peroxide generated.

8 Claims, 8 Drawing Sheets

(56) References Cited

OTHER PUBLICATIONS

International Search Report PCT/JP2010/068883 dated Nov. 22, 2010.

Masahiko Okada et al., "Direct Measurement of HDL Cholesterol: Method Eliminating Apoliprotein E-Rich Particles", Journal of Clinical Laboratory Analysis 15:223-229 (2001).

Hiroyuki Sugiuchi et al., "Comparison of Specificity of Three Homogenous LDL-cholesterol Methods for Cholesterol in Lp(a) and ApoE-rich Lipoprotein Fractions", Japanese Journal of Clinical Laboratory Automation, 2000, vol. 25, No. 2, pp. 104-110, pp. 109 last paragraph to p. 110 first paragraph.

Hiroyuki Sugiuchi Ph.D. et al., "Development of Homogeneous Assay for HDL-C in Serum", The Japanese Journal of Clinical Pathology, 2002, vol. 50, pp. 226-223.

Hiroshi Chiba et al., "A Rapid and Simple Quantification of Human Apoliprotein E-Rich High-Density Lipoproteins in Serum", Biochemical Medicine and Metabolic Biology, 47, 31-37 (1992).

Hitoshi Chiba, "Apolipoprotein E-Rich High Density Lipoprotein (HDL) and Measurement of HDL-Cholesterol", Seibutsu Shiryo Bunseki, 1996, vol. 19, No. 5, pp. 328-335.

Yoshiaki Katayama, "New Method for Homogeneous Assay of Serum High-Density Lipoprotein cholesterol Based on Unique Combination of Detergents—selective inhibition-", Seibutsu Shiryo Buseki, 1996, vol. 19, No. 5, pp. 340-345.

EP Application No. 10826682.6 Supplemental Search Report dated May 8, 2013.

\* cited by examiner

Fig. 2-1

Surfactants having an apoE-containing HDL response rate/apoE-deficient HDL response rate ratio of 1.3 or more and capable of assaying apoE-containing HDL

| Surfactant name | Type | Chemical name | ApoE-containing HDL response rate/apoE-deficient HDL response rate ratio | HLB |
|---|---|---|---|---|
| Nonion NS-202S | Nonionic | | 1.43 | |
| Adekatol PC-1 | Nonionic | Specific phenol ethoxylate | 1.42 | |

Surfactants having an apoE-containing HDL response rate/apoE-deficient HDL response rate ratio of 0.7 to less than 1.3 and capable of assaying both subfractions

| Surfactant name | Type | Chemical name | ApoE-containing HDL response rate/apoE-deficient HDL response rate ratio | HLB |
|---|---|---|---|---|
| Sintrex EH-R | Anionic | 2-Ethylhexyl sulfate sodium salt | 1.15 | |
| Neopelex No.1-F | Anionic | Alkyl benzene sulfonic acid | 1.10 | |
| Neopelex No.25 | Anionic | | 1.06 | |
| Emulgen 709 | Nonionic | Polyoxyethylene alkyl ether | 1.03 | 13.3 |
| Plonon 102 | Nonionic | Polyethylene glycol-polypropylene glycol-polyethylene glycol | 1.03 | |
| Adekatol LB-83 | Nonionic | Lauryl alcohol alkoxylate | 1.02 | |
| Neopelex G-65 | Anionic | High-grade sodium alkyl benzene sulfonate (soft type) | 1.01 | |
| Newrex Paste H | Anionic | Sodium alkyl benzene sulfonate | 1.01 | |
| Adekatol LB-93 | Nonionic | Lauryl alcohol alkoxylate | 0.97 | |
| Neopelex G-65 | Anionic | High-grade sodium alkyl benzene sulfonate (soft type) | 0.97 | |
| Emal NC-35 | Anionic | | 0.97 | |

Fig. 2-2

| | | | | |
|---|---|---|---|---|
| Naimin L-202 | Nonionic | Polyoxyethylene laurylamine | 0.97 | |
| Nonipole 120 | Nonionic | Polyoxyethylene nonylphenyl ether (n = about 12) | 0.96 | 6.2 |
| Nonion NS-212 | Nonionic | Polyoxyethylene nonylphenyl ether | 0.96 | 14.1 |
| Adekatol LB-103 | Nonionic | Lauryl alcohol alkoxylate | 0.95 | |
| Nissan Anon LG | Amphoteric | | 0.95 | |
| Adekatol NP-695 | Nonionic | Polyoxyethylene nonylphenyl ether | 0.95 | |
| Nissan Anon GLM-R-LV | Amphoteric | 2-Alkyl-1-N-carboxymethyl-N-hydroxyethyl-imidazolium betaine | 0.94 | |
| Nonipole 95 | Nonionic | Polyoxyethylene nonylphenyl ether (n = about 9.5) | 0.94 | |
| Adekatol NP-700 | Nonionic | Polyoxyethylene nonylphenyl ether | 0.94 | |
| Adekatol LB70 | Nonionic | Lauryl alcohol alkoxylate | 0.94 | |
| Soft Sen-oh 5S | | | 0.94 | |
| Nonipole 100 | Nonionic | Polyoxyethylene nonylphenyl ether (n = about 10) | 0.94 | |
| Ou-sen A | | | 0.94 | |
| Newrex Powder F | Anionic | | 0.93 | |
| Nonion LT-221 | Nonionic | Polyoxyethylene sorbitan monolaurate | 0.93 | 16.7 |
| Newrex Soft 30 | Anionic | Linear sodium alkyl benzene sulfonate | 0.93 | |
| Newrex Soft 60-N | Anionic | Linear sodium alkyl benzene sulfonate | 0.93 | |
| Dispanol K-3 | Nonionic | Specific ether type | 0.93 | |
| Sen-oh S | | | 0.93 | |
| Nonion O-6 | Nonionic | Polyoxyethylene monooleate | 0.92 | 13.7 |
| Amphitol 24B | Amphoteric | Lauryl dimethyl aminoacetic acid betaine | 0.91 | |
| Nonipole 130 | | | 0.91 | |
| Nonipole 85 | Nonionic | Polyoxyethylene nonylphenyl ether | 0.91 | |
| Nonion L-4 | Nonionic | Polyoxyethylene monolaurate | 0.89 | 13.3 |
| Leodol TW-L120 | Nonionic | Polyoxyethylene sorbitan mono-coconut oil fatty acid ester | 0.88 | 16.7 |
| Nonion MN-811 | Nonionic | | 0.87 | |
| Diapon S | Anionic | Sodium fatty acid methyl taurate | 0.87 | |
| Persoft SL | Anionic | | 0.87 | |
| Leodol TW-L120 | Nonionic | Polyoxyethylene sorbitan mono-coconut oil fatty acid ester | 0.87 | 16.7 |
| Nonion HS-210 | Nonionic | | 0.87 | |
| Persoft NK-60 | Nonionic | Polyoxyethylene alkyl ether | 0.87 | 12 |
| Nonion NS-210 | Nonionic | Polyoxyethylene nonylphenyl ether | 0.87 | 13.3 |

Fig. 2-3

| | | | |
|---|---|---|---|
| Nissan Anon BF | Amphoteric | Alkyldimethyl aminoacetic acid betaine | 0.86 |
| Pelex SS-H | Anionic | Sodium alkyl diphenyl ether disulfonate | 0.86 |
| Trux H-45 | Anionic | | 0.86 |
| Emal A | Anionic | Sodium alkylsulfate | 0.86 |
| Pelex NBL | Anionic | Sodium alkyl naphthalene sulfonate | 0.85 |
| Trux H-45W | Anionic | | 0.85 |
| Plonon 204 | Nonionic | Polyethylene glycol-polypropylene glycol-polyethylene glycol | 0.85 |
| Sunbase | Anionic | Sodium salt of alpha-sulfonated methyl ester of fatty acid | 0.84 |
| Persoft SF-T | Anionic | Triethanolamine salt of alkyl sulfate | 0.84 |
| Nissan Anon BDF-SF | Amphoteric | Coconut oil fatty acid amide propyl dimethylaminoacetic acid betaine | 0.83 |
| Adekamin 4MAC-30 | | | 0.83 |
| Nonion S15-4 | Nonionic | Polyoxyethylene monostearate | 0.81 | 16.9 |
| Sunamide C-3 | Anionic | Sodium salt of fatty acid amide ether sulfate | 0.81 |
| Nonion HS-208 | Nonionic | | 0.81 |
| Neopelex GS | Anionic | Unneutralized alkylbenzene sulfonic acid (soft type) | 0.80 |
| Succineed 3LN | | | 0.80 |
| Sunamide CF-3 | Anionic | Sodium salt of fatty acid amide ether sulfate | 0.79 |
| Naimin T2-210 | Nonionic | Polyoxyethylene beef tallow alkylamine | 0.79 | 12.5 |
| Persoft NK-100 | Nonionic | Polyoxyethylene alkyl ether | 0.78 | 14 |
| Emal E-27C | Anionic | | 0.78 |
| Emal 20T | Anionic | Triethanolamine polyoxyethylene alkyl ether sulfate | 0.78 |
| Sunamide CF-10 | Anionic | Sodium salt of fatty acid amide ether sulfate | 0.78 |
| Leodol TW-S120 | Nonionic | Polyoxyethylene sorbitan monostearate | 0.78 | 14.9 |
| Emulgen 1118S-70 | Nonionic | Polyoxyethylene alkyl ether | 0.77 | 16.4 |
| Emal 20CM | Anionic | Sodium polyoxyethylene alkyl ether sulfate | 0.77 |
| Levenol WZ | Anionic | Sodium polyoxyethylene alkyl ether sulfate | 0.77 |
| Emulgen 120 | Nonionic | Polyoxyethylene lauryl ether | 0.76 | 15.3 |
| Polystar OMP | Amphoteric | Sodium salt of a polymeric carboxylic acid | 0.76 |
| Adekacol CS-141E | Anionic | Phosphoric ester | 0.76 |
| Adekacol CS-141E | Anionic | Aromatic phosphoric ester | 0.75 |
| Sunbase | Anionic | Sodium salt of alpha-sulfonated methyl ester of fatty acid | 0.75 |

Fig. 2-4

| Surfactant name | Type | Chemical name | | |
|---|---|---|---|---|
| Emulgen LS-114 | Nonionic | Higher alcohol ester type | 0.75 | 14 |
| Emanon CH-40 | Nonionic | Polyoxyethylene hydrogenated castor oil | 0.74 | 12.5 |
| Persoft EL | Anionic | Sodium salt of polyoxyethylene alkyl sulfate | 0.73 | |
| Nonion NS-230 | Nonionic | Polyoxyethylene nonylphenyl ether | 0.73 | 17.1 |
| Adekatol LB-1520 | Nonionic | Lauryl alcohol alkoxylate | 0.72 | |
| NaiminDT-203 | Nonionic | Polyoxyethylene alkyl propylenediamine | 0.72 | 6 |
| Persoft EP | Anionic | Sodium salt of polyoxyethylene lauryl sulfate | 0.71 | |
| Nonion HS-220 | Nonionic | Polyoxyethylene octyl phenyl ether | 0.71 | 16.2 |
| Persoft SP | Anionic | Sodium salt of lauryl sulfate | 0.70 | |

Surfactants having an apoE-containing HDL response rate/apoE-deficient HDL response rate ratio of less than 0.7 and capable of assaying apoE-containing HDL

| Surfactant name | Type | Chemical name | ApoE-containing HDL response rate/apoE-deficient HDL response rate ratio | HLB |
|---|---|---|---|---|
| Nonion NS-220 | Nonionic | Polyoxyethylene nonylphenyl ether | 0.69 | 16 |
| Persoft EF | Anionic | Sodium salt of polyoxyethylene alkyl sulfate | 0.69 | |
| Triton WR-1339 | | | 0.68 | |
| Adekacol PS-440E | Anionic | Aliphatic phosphoric ester | 0.66 | |
| Trux K-40 | | | 0.66 | |
| Naimin F-215 | Nonionic | Polyoxyethylene alkyl(coconut)amine | 0.66 | 15.6 |
| Nissan Anon BL-SF | Amphoteric | Lauryl dimethyl aminoacetic acid betaine | 0.66 | |
| Adekatol LB-1220 | Nonionic | Lauryl alcohol alkoxylate | 0.65 | |
| Nonion OT-221 | Nonionic | Polyoxyethylene sorbitan monooleate | 0.65 | 15.7 |
| Nissan Anon BL | Amphoteric | Lauryl dimethyl aminoacetic acid betaine | 0.64 | |
| Nonion NS-215 | Nonionic | Polyoxyethylene nonylphenyl ether | 0.62 | 15 |
| Naimin S-220 | Nonionic | Polyoxyethylene stearylamine | 0.61 | 15.4 |
| Nonion HS-215 | Nonionic | Polyoxyethylene octyl phenyl ether | 0.61 | 15 |
| Naimin S-210 | Nonionic | Polyoxyethylene stearylamine | 0.60 | 12.8 |
| Naimin T2-230 | Nonionic | Polyoxyethylene beef tallow alkylamine | 0.58 | 16.5 | y = 0.858x + 7.8
r = 0.951
n = 18 y = 0.866x + 9.6
r = 0.936
n = 18

METHOD FOR ASSAYING CHOLESTEROL IN APOE-CONTAINING HDL

CLAIM TO CONVENTION PRIORITY

This application is the U.S. National Phase of PCT/JP2010/068883 filed Oct. 26, 2010, which claims priority from Japanese Patent Application No. 2009-245476 filed Oct. 26, 2009. The disclosure of each of these applications is incorporated by reference in their entireties.

TECHNICAL FIELD

The present invention relates to a method for separately quantifying a cholesterol (-C) subfraction in high density lipoprotein (HDL).

BACKGROUND ART

It is known that HDL receives cholesterol from various tissues, including the walls of blood vessels with arterial sclerosis, and it is thus associated with removal of cholesterol accumulated in cells. Also, HDL is a preventive factor for onset of various arteriosclerotic diseases, including coronary artery sclerosis, and the HDL level in the blood serves as a useful indicator for onset of an arteriosclerotic disease.

HDL is a composite of lipid components, such as a protein referred to as an "apoprotein," phospholipid, cholesterol, and neutral fat. One such lipid component is apolipoprotein E (apoE), and HDL can be classified as an apoE-containing HDL subfraction or an apoE-deficient HDL subfraction based on apoE content. ApoE-containing HDL has strong cholesterol efflux capacity and anti-platelet effects, and, among various types of HDLs, it has drawn attention as a very good lipoprotein. In recent years, a CETP inhibitor that elevates HDL-C has been expected as a lipid-lowering agent following statin. CETP inhibitors are known to mainly elevate the apoE-containing HDL among various types of HDLs.

As methods for assaying cholesterol in HDL, for example, a method comprising separating HDL from other lipoproteins via ultracentrifugation and assaying cholesterol and a method comprising separating HDL via electrophoresis and staining lipids to assay the intensity of color development have been known. These methods, however, are disadvantageous due to complicated procedures, the incapability of simultaneous processing of many test samples, and other problems. Thus, such methods are hardly ever employed on a routine basis.

An example of a method for assaying cholesterol in HDL is a method comprising adding a precipitating agent to a test sample to coagulate lipoproteins other than HDL, removing the resulting coagulate via centrifugation, and assaying cholesterol in the supernatant selectively containing the separated HDL. According to such method, reactivity to an HDL subfraction is known to vary depending on the type of precipitating agent used. According to a method involving the use of phosphotungstic acid-magnesium, dextran sulfate-magnesium, or heparin-calcium as a precipitating agent, apoE-containing HDL coagulates with lipoproteins, such as VLDL and LDL, and it is removed as a precipitated fraction via centrifugation. Thus, apoE-containing HDL cannot be assayed as an HDL fraction. According to a method involving the use of heparin-manganese or polyethylene glycol (PEG), apoE-containing HDL does not coagulate, and it is assayed as HDL. While a method involving the use of a precipitating agent to separately quantify HDL can be carried out more simply than ultracentrifugation or electrophoresis, this method comprises addition of a precipitating agent and separation. Thus, it is insufficient in terms of convenience and the necessity for relatively large quantities of test samples.

In recent years, a method of quantification of HDL-C with the use of an automatic analyzer without pretreatment with a precipitating agent has been known as a simple method of HDL-C quantification. For example, a method in which cholesterol esterase or cholesterol oxidase is chemically modified and cholesterol in HDL is captured in a specific manner in the presence of an inclusion compound, such as cyclodextrin (see Patent Document 1), a method in which a coagulate or complex with lipoproteins other than HDL is formed and cholesterol in HDL is then captured via an enzymatic reaction (see Patent Documents 2 and 3), and a method involving the use of a surfactant with an HLB of 13 to 14, which specifically acts on HDL (see Patent Document 4), have been known.

PRIOR ART DOCUMENTS

Patent Documents

[Patent Document 1] JP Patent Publication (Kokai) No. H-07-301636 A (1995)
[Patent Document 2] JP Patent Publication (Kokai) No. H-08-131197 A (1996)
[Patent Document 3] JP Patent Publication (Kokai) No. H-08-201393 A (1996)
[Patent Document 4] WO 98/26090

SUMMARY OF THE INVENTION

Object to be Attained by the Invention

The methods described above allow HDL cholesterol (HDL-C) to be assayed, although reactivity with each HDL subfraction varies. When HDL is divided into subfractions, apoE-deficient HDL cholesterol (apoE-deficient HDL-C) and apoE-containing HDL cholesterol (apoE-containing HDL-C) cannot be partially or substantially assayed. That is, such methods do not allow apoE-deficient HDL-C and apoE-containing HDL-C to be separately quantified.

The present invention is intended to provide a method for separately (fractionally) or simultaneously quantifying cholesterol in total HDL, cholesterol in an HDL subfraction of apoE-containing HDL, and cholesterol in an HDL subfraction of apoE-deficient HDL without the necessity for complicated fragmentation and separation procedures.

Means for Attaining the Object

The present inventors have conducted concentrated studies. As a result, they discovered surfactants exhibiting different levels of activity (i.e., reactivity) with HDL subfractions of apoE-containing HDL and apoE-deficient HDL. By using such surfactants exhibiting different reactivity according to need, apoE-containing HDL-C and apoE-deficient HDL-C can be separately or fractionally assayed, and total HDL-C (i.e., both apoE-containing HDL-C and apoE-deficient HDL-C) can also be assayed. The present inventors discovered that, when assay is carried out in two steps with the use of a general automatic analyzer involving the use of two reagents, use of surfactants in combination with the first reagent used in the first step and with the second reagent used in the second step would enable separate or fractional assay of apoE-containing HDL-C, apoE-deficient HDL-C, and total HDL-C and would further enable simultaneous assay of a plurality of any thereof. The present invention has been completed based on such findings.

Accordingly, the present invention provides a method for quantifying HDL-C subfractions that allows separate quantification of an HDL subfraction of apoE-containing HDL-C and of apoE-deficient HDL-C in a test sample, as well as simultaneous assay of both thereof.

Specifically, the present invention is as follows.

[1] A method of enzymatically and separately quantifying cholesterol in apoE-containing HDL and/or cholesterol in apoE-deficient HDL by adding a surfactant selected from the group consisting of a surfactant with an apoE-containing HDL response rate/apoE-deficient HDL response rate ratio of 0.7 to less than 1.3, a surfactant with an apoE-containing HDL response rate/apoE-deficient HDL response rate ratio of less than 0.7, and a surfactant with an apoE-containing HDL response rate/apoE-deficient HDL response rate ratio of 1.3 or more to a test sample, allowing cholesterol esterase and cholesterol oxidase to react therewith, and quantifying the hydrogen peroxide generated.

[2] A method of enzymatically quantifying cholesterol in a total amount of HDL, including cholesterol in apoE-containing HDL, by adding a surfactant with an apoE-containing HDL response rate/apoE-deficient HDL response rate ratio of 0.7 to less than 1.3 to a test sample, allowing cholesterol esterase and cholesterol oxidase to react therewith, and quantifying the hydrogen peroxide generated.

[3] A method of selectively and enzymatically quantifying cholesterol in apoE-deficient HDL by adding a surfactant with an apoE-containing HDL response rate/apoE-deficient HDL response rate ratio of less than 0.7 to a test sample, allowing cholesterol esterase and cholesterol oxidase to react therewith, and quantifying the hydrogen peroxide generated.

[4] A method of selectively and enzymatically quantifying cholesterol in apoE-containing HDL by adding a surfactant with an apoE-containing HDL response rate/apoE-deficient HDL response rate ratio of 1.3 or more to a test sample, allowing cholesterol esterase and cholesterol oxidase to react therewith, and quantifying the hydrogen peroxide generated.

[5] A method of quantifying cholesterol in apoE-containing HDL by subtracting the value of cholesterol in apoE-deficient HDL determined by the method according to [3] from the value of total cholesterol including cholesterol-containing HDL and apoE-containing HDL determined by the method according to [2] to determine the cholesterol level in apoE-containing HDL.

[6] The method of quantifying cholesterol in HDL according to [1] or [2], wherein the surfactant with an apoE-containing HDL response rate/apoE-deficient HDL response rate ratio of 0.7 to less than 1.3 is Dispanol K3.

[7] The method of quantifying cholesterol in HDL according to [1] or [3], wherein the surfactant with an apoE-containing HDL response rate/apoE-deficient HDL response rate ratio of less than 0.7 is Adekatol LB-1220.

[8] The method of quantifying cholesterol in HDL according to [1] or [4], wherein the surfactant with an apoE-containing HDL response rate/apoE-deficient HDL response rate ratio of 1.3 or more is Nonion NS-202S.

[9] The method of quantifying cholesterol in HDL according to any of [1] to [8], which comprises a first step of erasing cholesterol in lipoproteins other than HDL in a test sample and a second step of quantifying cholesterol in HDL.

[10] A method of quantifying cholesterol in apoE-containing HDL comprising: a first step of adding a surfactant with an apoE-containing HDL response rate/apoE-deficient HDL response rate ratio of less than 0.7 to a test sample, allowing the surfactant to selectively react with apoE-deficient HDL, and leading cholesterol in apoE-deficient HDL to the outside of the reaction system with the action of cholesterol esterase, cholesterol oxidase, and catalase; and a second step of adding a surfactant with an apoE-containing HDL response rate/apoE-deficient HDL response rate ratio of 0.7 to less than 1.3 or a surfactant with an apoE-containing HDL response rate/apoE-deficient HDL response rate ratio of 1.3 or more, and allowing the surfactant to react with remaining HDL in a test sample to quantify cholesterol in apoE-containing HDL.

[11] A method of simultaneously quantifying cholesterol in apoE-containing HDL and cholesterol in total amount of HDL comprising: a first step of adding a surfactant with an apoE-containing HDL response rate/apoE-deficient HDL response rate ratio of less than 0.7 to a test sample and generating hydrogen peroxide derived from cholesterol in apoE-deficient HDL; and a second step of detecting the hydrogen peroxide derived from cholesterol in apoE-deficient HDL at an early stage and simultaneously adding a surfactant with an apoE-containing HDL response rate/apoE-deficient HDL response rate ratio of 0.7 to less than 1.3 or a surfactant with an apoE-containing HDL response rate/apoE-deficient HDL response rate ratio of 1.3 or more and detecting the hydrogen peroxide derived from cholesterol in apoE-containing HDL.

This description includes part or all of the contents as disclosed in the description and/or drawings of Japanese Patent Application No. 2009-245476, which is a priority document of the present application.

Effects of the Invention

The method of the present invention enables separate or fractional quantification of cholesterol in an HDL subfraction such as cholesterol in apoE-containing HDL and cholesterol in apoE-deficient HDL by adequately using a surfactant with an apoE-containing HDL response rate/apoE-deficient HDL response rate ratio of 0.7 to less than 1.3, a surfactant with an apoE-containing HDL response rate/apoE-deficient HDL response rate ratio of less than 0.7, or a surfactant with an apoE-containing HDL response rate/apoE-deficient HDL response rate ratio of 1.3 or more to enzymatically process a test sample and quantifying the hydrogen peroxide generated. In addition, cholesterol in an HDL subfraction and cholesterol in the total amount of HDL can be simultaneously quantified.

BRIEF DESCRIPTION OF THE DRAWINGS

FIG. 2-1 shows the apoE-containing HDL response rate/apoE-deficient HDL response rate ratio in an HDL subfraction assayed by the method of Example 1 according to the present invention.

FIG. 2-2 shows the apoE-containing HDL response rate/apoE-deficient HDL response rate ratio in an HDL subfraction assayed by the method of Example 1 according to the present invention (continued from FIG. 2-1).

FIG. 2-3 shows the apoE-containing HDL response rate/apoE-deficient HDL response rate ratio in an HDL subfraction assayed by the method of Example 1 according to the present invention (continued from FIG. 2-2).

FIG. 2-4 shows the apoE-containing HDL response rate/apoE-deficient HDL response rate ratio in an HDL subfraction assayed by the method of Example 1 according to the present invention (continued from FIG. 2-3).

FIG. 3 shows reactivity to various lipoproteins assayed by the method of Example 2 according to the present invention.

FIG. 4 shows the correlation between the method of Example 3 according to the present invention and the PT-DS-Mg precipitation method.

EMBODIMENTS FOR CARRYING OUT THE INVENTION

Figure 1:
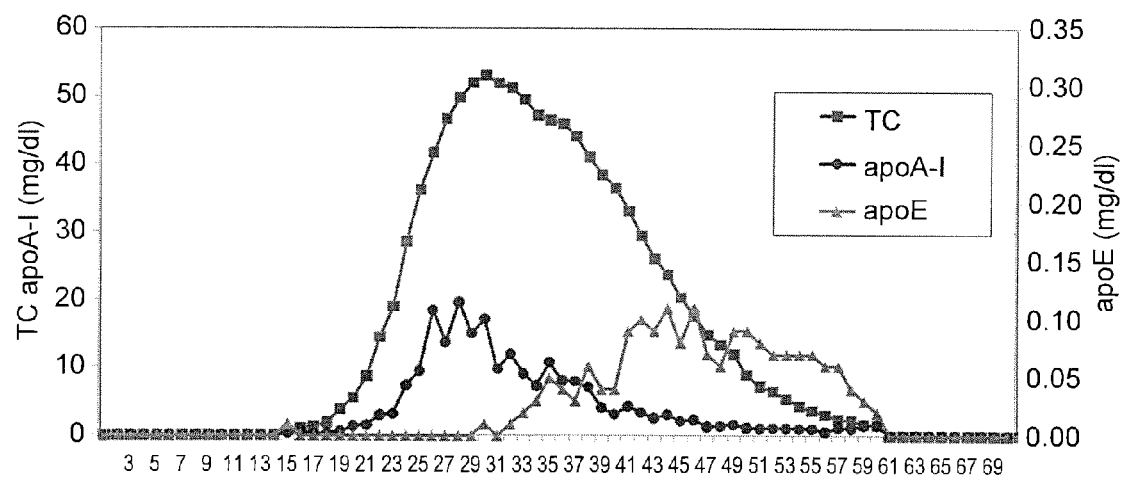
FIG. 1 shows apoE-deficient HDL and apoE-containing HDL fractions separated by the method of Reference Example 1 according to the present invention.

Hereafter, the present invention is described in detail.

The present invention concerns a method of quantifying apoE-containing HDL-C and apoE-deficient HDL-C in a test sample.

Cholesterol contained in lipoproteins is classified as esterified cholesterol (cholesterol ester) or free cholesterol. The term "cholesterol" used herein refers to either thereof.

A lipoprotein can be roughly divided into VLDL, LDL, and HDL fractions. HDL can be divided into apoE-containing HDL and apoE-deficient HDL subfractions based on apoE content. In general, the term "apoE-containing HDL" refers to a fraction that contains apoE in HDL and the term "apoE-deficient HDL" refers to a fraction that does not contain apoE. HDL is divided into apoE-containing HDL and apoE-deficient HDL subfractions because the action mechanisms of such lipoproteins on arteriosclerosis are different, and it is thus necessary to separately assay such fractions. Specifically, apoE-containing HDL has strong cholesterol efflux capacity and anti-platelet effects, and it functions as a "good" cholesterol among HDLs. In addition, a CETP inhibitor that elevates the HDL-C level as a lipid-lowering agent is known to mainly elevate the apoE-containing HDL level.

HDL in which apoE is present or HDL containing large quantities of apoE is occasionally referred to as "apoE-rich HDL," and such apoE-rich HDL is within the scope of apoE-containing HDL.

Since apoE content is continuously distributed within HDL, it is difficult to clearly distinguish apoE-containing HDL from apoE-deficient HDL based on apoE content in a lipoprotein. When HDL is fractionated via chromatography or other means using apoE content as an indicator as described below, apoE content is determined, and apoE-containing HDL may be distinguished from apoE-deficient HDL based on the determined value.

In addition, HDL can be classified as HDL2 or HDL3 depending on differences in density, and HDL2 and HDL3 each have apoE-containing HDL 2 and apoE-containing HDL 3 with different apoE content. Some HDLs having a large particle size lack apolipoprotein A1 (apoA1), which is generally present, but contain large quantities of apoE, and such HDLs are also within the scope of apoE-containing HDL. Diameters of lipoprotein particles vary depending on the persons reporting such diameters, and diameters of VLDL are from 30 nm to 80 nm (30 nm to 75 nm), those of LDL are from 22 nm to 28 nm (19 nm to 30 nm), and those of HDL are from 7 nm to 10 nm. The density of VLDL is 1.006 or less, that of LDL is from 1.019 to 1.063, and that of HDL is from 1.063 to 1.21.

Any test samples can be subjected to assays by the method of the present invention, provided that such test samples may contain lipoproteins, such as HDL, LDL, VLDL, or CM. Examples thereof include, but are not limited to, body fluid samples, such as blood serum or plasma samples, and dilution products thereof.

The method of the present invention is generally carried out with the use of an automatic analyzer. The number of steps carried out in the method of the present invention is not limited, and the method is preferably carried out through two steps (the first step and the second step).

In the first step, for example, lipoproteins other than HDL, such as CM, VLDL, and LDL, HDL subfractions other than HDL subfractions, which are to be assayed, among HDL subfractions of apoE-containing HDL and apoE-deficient HDL are led to the outside of the reaction system. Specifically, cholesterol esterase is allowed to react with a test sample, and the resulting cholesterol is allowed to react in the presence of an enzyme reactive to, such as cholesterol oxidase or cholesterol dehydrogenase, to lead cholesterol to the outside of the reaction system. In such a case, the reaction may be carried out in the presence of a given surfactant having reactivity with a lipoprotein to be led to the outside of the reaction system.

In this description, the action of leading cholesterol in a lipoprotein to the outside of the reaction system involves erasing or coagulation of cholesterol contained in the lipoprotein or inhibition of the same so as to block cholesterol from undergoing a reaction in the subsequent step, so as to prevent cholesterols contained in a lipoprotein, such as CM, VLDL, LDL, and an HDL subfraction, other than the assay target from influencing quantification of HDL-C or subfraction HDL-C as an assay target.

The term "erasing" used herein refers to degradation of lipoprotein cholesterol in a test sample that makes the degradation product undetectable in the subsequent step. An example of a method for erasing lipoprotein cholesterol is a method comprising allowing cholesterol esterase and cholesterol oxidase to react with lipoprotein cholesterol and degrading the generated hydrogen peroxide into water and oxygen with the use of catalase. Alternatively, a hydrogen donor may be allowed to react with generated hydrogen peroxide with the use of peroxidase to convert the product into colorless quinone. It should be noted that lipoprotein cholesterol erasing is not limited thereto.

In the second step, cholesterol esterase is allowed to react with a test sample in the presence of a surfactant having reactivity with the assay target, the resulting cholesterol is subjected to a reaction in the presence of a cholesterol-reactive enzyme, such as cholesterol oxidase or cholesterol dehydrogenase, to convert the generated hydrogen peroxide into a quinone pigment, and the resulting quinone pigment is assayed. Thus, the assay target can be enzymatically quantified.

The HDL subfractions of apoE-containing HDL and apoE-deficient HDL according to the present invention can be fractionated in the following manner. As described in the reference examples below, for example, an HDL-containing sample is subjected to ultracentrifugation using potassium bromide to separate all lipoproteins, HDL is separated by coagulating lipoproteins other than HDL with the use of polyethylene glycol, and HDL subfractions are fractionated via gradient elution using sodium chloride via heparin affinity chromatography. Thus, the apoE-deficient HDL fraction and the apoE-containing HDL fraction can be separated.

With the use of apoE-containing HDL and apoE-deficient HDL subfractions thus fractionated, the reactivity of various surfactants with HDL subfractions of apoE-containing HDL and apoE-deficient HDL can be inspected. The reactivity of a surfactant with a lipoprotein can be evaluated using the degree of cholesterol reaction as an indicator when cholesterol esterase and cholesterol oxidase are allowed to react with a lipoprotein in the presence of the surfactant. Specifically, various surfactants are incorporated into the second reagent and reactivity of the surfactants with a lipoprotein can be assayed in the manner described in Example 1, for example.

With the use of the HDL subfraction fractionated as described above, the reactivity of various surfactants can be analyzed and examined in the manner described above. In this description, the intensity of the reaction of a surfactant may be represented in terms of a response rate or a ratio thereof. Specifically, the level of reaction of a surfactant with apoE-containing HDL and that of a surfactant with apoE-deficient HDL are assayed, and the ratio thereof with respect to the total amount of cholesterol in a sample (hereafter, referred to as "the apoE-containing HDL response rate/apoE-deficient HDL response rate ratio") may be determined. Thus, the apoE-containing HDL response rate/apoE-deficient HDL response rate ratio can be determined.

Thus, surfactants are classified as follows: a surfactant having reactivity with both apoE-containing HDL and apoE-deficient HDL (with an apoE-containing HDL response rate/apoE-deficient HDL response rate ratio of 0.7 to less than 1.3); a surfactant having strong reactivity with apoE-containing HDL but weak reactivity with apoE-deficient HDL (with an apoE-containing HDL response rate/apoE-deficient HDL response rate ratio of 1.3 or more); and a surfactant having strong reactivity with apoE-deficient HDL but weak reactivity to apoE-containing HDL (with an apoE-containing HDL response rate/apoE-deficient HDL response rate ratio of less than 0.7). Classification of surfactants is shown in FIG. 2-1 to FIG. 2-4.

Examples of the surfactants having reactivity with both apoE-containing HDL and apoE-deficient HDL (i.e., surfactants having strong reactivity with both types of HDL) include a surfactant with an apoE-containing HDL response rate/apoE-deficient HDL response rate ratio of 0.7 to less than 1.3 and, preferably, a surfactant with an apoE-containing HDL response rate/apoE-deficient HDL response rate ratio of 0.8 to less than 1.2. An example of an anionic surfactant is sodium alkylbenzene sulfonate, examples of nonionic surfactants include polyoxyethylene monolaurate, lauryl alcohol alkoxylate, polyoxyethylene laurylamine, a polyoxyethylene-polyoxypropylene block polymer having a molecular weight of less than 1,700, and polyoxyethylene nonylphenyl ether having an HLB of 13.0 to less than 14.5, and examples of amphoteric surfactants include alkyldimethyl aminoacetic acid betaine and alkyl carboxymethyl hydroxyethyl imidazolium betaine. Specific examples of anionic surfactants include Newrex Soft 60-N, Newrex Powder F, and Newrex Paste H (NOF Corporation), and Neopelex No. 1-F, Neopelex G-65, and Emal NC-35 (Kao Corporation). Specific examples of nonionic surfactants include Adekatol LB70, Adekatol LB-103, and Adekatol LB-93 (Adeka Corporation), Dispanol K-3, Nonion L-4, Nonion MN-811, Nonion NS-210, Nonion NS-212, Naimin L-202, Plonon 102, and Plonon 204 (NOF Corporation), and Nonipole 85, Nonipole 95, Nonipole 100, and Nonipole 120 (Sanyo Chemical Industries, Ltd.). Specific examples of amphoteric surfactants include Amphitol 24B (Kao Corporation), Nissan Anon BF, Nissan Anon GLM-R-LV, and Nissan Anon LG (NOF Corporation).

Examples of surfactants with strong reactivity with apoE-containing HDL but weak reactivity with apoE-deficient HDL include a surfactant with an apoE-containing HDL response rate/apoE-deficient HDL response rate ratio of 1.3 or more, and, preferably, a surfactant with an apoE-containing HDL response rate/apoE-deficient HDL response rate ratio of 1.4 or more. An example thereof is polyoxyethylene nonylphenyl ether having an HLB of 5 to 6 (e.g., 5.7), and a specific example is Nonion NS-202S (tradename: NOF Corporation).

Examples of surfactants with strong reactivity with apoE-deficient HDL but weak reactivity with apoE-containing HDL include a surfactant with an apoE-containing HDL response rate/apoE-deficient HDL response rate ratio of less than 0.7, and, preferably, a surfactant with an apoE-containing HDL response rate/apoE-deficient HDL response rate ratio of less than 0.65. Examples of such anionic surfactants include sodium polyoxyethylene alkyl ether sulfate, triethanolamine polyoxyethylene alkyl ether sulfate, sodium salt of fatty acid amide ether sulfate, lauryl alcohol alkoxylate with a clouding point of 75° C. or higher, higher alcohol ether, aromatic phosphate ester, aliphatic phosphate ester, and polyoxyethylene octyl phenyl ether or polyoxyethylene nonylphenyl ether having an HLB of 15 to less than 17.5. Specific examples of anionic surfactants include Emal 20CM, Emal 20T, and Levenol WZ (Kao Corporation), Sunamide C-3 and Sunamide CF-10 (NOF Corporation), and Adekacol CS-141E and Adekacol PS-440E (Adeka Corporation). Specific examples of nonionic surfactants include Nonion HS-215, Nonion NS-215, Nonion HS-220, Nonion NS-220, Nonion NS-230, and Naimin T2-210 (NOF Corporation), Emulgen 1118S-70, Emulgen 120, and Emulgen LS-114 (Kao Corporation), and Adekatol LB-1220 and Adekatol LB-1520 (Adeka Corporation).

Hereafter, the method of the present invention for separately quantifying an HDL subfraction of cholesterol in an HDL subfraction such as cholesterol in apoE-containing HDL and apoE-deficient HDL and simultaneously assaying both thereof with the use of the aforementioned surfactants is described.

As described above, the method of the present invention can comprise the first step and the second step, and the reactions described below may be implemented in the first step and the second step.

(1) Lipoproteins other than HDL (i.e., CM, VLDL, and LDL) are erased in the first step and apoE-containing HDL and/or apoE-deficient HDL cholesterol is assayed in the second step.

(2) ApoE-containing HDL or apoE-deficient HDL is erased in the first step and the remaining apoE-containing HDL or apoE-deficient HDL cholesterol is assayed in the second step. In such a case, lipoproteins other than HDL (i.e., CM, VLDL, and LDL) may or may not be erased in the first step.

According to the method of the present invention, a surfactant having reactivity with apoE-containing HDL and apoE-deficient HDL can be used in both of the first step and the second step. In such a case, surfactant concentration is preferably 0.05 g/l to 2.0 g/l and more preferably 0.1 g/l to 1.0 g/l in the first step, and it is preferably 0.15 g/l to 6.0 g/l and more preferably 0.3 g/l to 3.0 g/l in the second step.

When the surfactant having reactivity with apoE-containing HDL and apoE-deficient HDL is used in the second step, lipoproteins other than HDL, such as CM, VLDL, and LDL, may be erased in the first step, and assay specificity with apoE-containing HDL and/or apoE-deficient HDL cholesterol can be improved.

Examples of methods for erasing lipoproteins other than HDL include a method involving the use of catalase and a method involving the formation of colorless quinone. In the absence of a surfactant that acts on HDL, cholesterol esterase and cholesterol oxidase are allowed to react with the test sample, and hydrogen peroxide derived from lipoproteins other than HDL is removed. Ester-type cholesterol in lipoprotein is hydrolyzed with the action of cholesterol esterase, and free cholesterol and fatty acid are generated. Subsequently, the generated free cholesterol and free cholesterol originally present in a lipoprotein are oxidized with the action of cholesterol oxidase, and cholestenone and hydrogen peroxide are generated. Lipoproteins can be eliminated by removing the resulting hydrogen peroxide. Examples of methods for removing hydrogen peroxide include, but are not limited to, a method comprising allowing catalase to act on hydrogen peroxide to degrade the same into water and oxygen and a method comprising allowing a phenol-based or aniline-based hydrogen donor compound, such as DAOS (N-ethyl-N-(2-hydroxysulfopropyl)-3,5-dimethoxyaniline), which reacts with hydrogen peroxide to yield a colorless quinone, to react with hydrogen peroxide to convert the hydrogen peroxide to the colorless quinone with the action of peroxidase.

Thus, most of the cholesterol in the lipoproteins other than HDL is erased in the first step, and cholesterol in HDL or HDL subfractions in apoE-containing HDL and/or apoE-deficient HDL is specifically quantified through the reaction in the second step.

The first step may be carried out in the absence of a surfactant that acts on HDL. Thus, substantially no cholesterol in HDL undergoes reactions, cholesterol in other lipoproteins, such as LDL, VLDL, or CM, selectively undergoes reactions, and such cholesterol is selectively erased. As a result, cholesterol in HDL or HDL subfractions in apoE-containing HDL and/or apoE-deficient HDL is selectively quantified in the subsequent second step.

The concentration of cholesterol esterase in the reaction solution used in the first step is preferably about 0.2 to 1.0 U/ml, and the concentration of cholesterol oxidase is preferably about 0.1 to 0.7 U/ml. The concentration of catalase is preferably about 40 to 100 U/ml, and the concentration of peroxidase is preferably about 0.4 to 1.0 U/ml. The concentration of the compound that yields the colorless quinone upon reaction with hydrogen peroxide is preferably about 0.4 to 0.8 mmol/l.

The reaction in the first step is preferably carried out in a buffer with a pH of 5 to 8, and the buffer is preferably a phosphate, glycine, Tris, or Good's buffer. Bis-Tris, PIPES, MOPSO, BES, HEPES, and POPSO, which are Good's buffer, are particularly preferable. The concentration of the buffer is preferably about 10 to 500 mM.

To enhance the efficiency of erasing of lipoproteins other than HDL in the first step, divalent metal ions may be contained in the reaction solution. Examples of divalent metal ions that can be preferably used include copper, iron, and magnesium ions, with magnesium ions being particularly preferable. The concentration of the divalent metal ions is preferably about 5 to 200 mM.

A lipoprotein hydrolase may optionally be added to the reaction solution used in the first step. Addition of this enzyme is preferable because cholesterol in VLDL, in particular, easily reacts. The concentration of this enzyme in the reaction solution is preferably about 5.0 to 10.0 U/ml.

The reaction temperature in the first step is preferably about 25° C. to 40° C., with 37° C. being the most preferable. The reaction time may be about 2 to 10 minutes.

When the surfactant that reacts both with apoE-containing HDL and apoE-deficient HDL is used in the second step, total HDL-C value can be obtained. The apoE-deficient HDL-C value determined with the use of the surfactant having strong reactivity with apoE-deficient HDL but weak reactivity with apoE-containing HDL may be subtracted from total HDL-C value to quantify apoE-containing HDL-C.

In addition, the surfactant having strong reactivity with apoE-deficient HDL but weak reactivity with apoE-containing HDL is added to a first reagent used in the first step of erasing the lipoproteins other than HDL, and the surfactant having reactivity with both apoE-containing HDL and apoE-deficient HDL or the surfactant having strong reactivity with apoE-containing HDL but weak reactivity with apoE-deficient HDL is added to a second reagent used in the second step. Thus, apoE-containing HDL-C can be accurately assayed.

In such a case, erasing of apoE-deficient HDL-C in the first step is sufficient. Cholesterol in lipoproteins such as CM, VLDL, or LDL may be erased in the first step. Alternatively, lipoproteins such as CM, VLDL, or LDL may not undergo reactions in either the first or second step, and they may remain unerased to the end.

When apoE-deficient HDL-C is erased in the first step, the concentration of the surfactant used in the first step must be lower than that of the surfactant used in the second step, so that the action of the surfactant having reactivity with both apoE-containing HDL and apoE-deficient HDL or the surfactant having strong reactivity with apoE-containing HDL but weak reactivity with apoE-deficient HDL used in the second step is not inhibited.

Specifically, the concentration rate of the surfactant used in the first step (in the first reagent) preferably has a value less than 0.2, and more preferably less than 0.1.

In the first step, further, the surfactant having strong reactivity with apoE-deficient HDL but weak reactivity with apoE-containing HDL is added, and the surfactant is allowed to act with cholesterol esterase and cholesterol oxidase in the absence of catalase. In the second step, the surfactant having reactivity with both apoE-containing HDL and apoE-deficient HDL or the surfactant having strong reactivity with apoE-containing HDL but weak reactivity with apoE-deficient HDL is added. Thus, both the apoE-containing HDL-C value and total HDL-C value can be determined with a single assay.

In such case, apoE-deficient HDL is degraded by a surfactant having strong reactivity with apoE-deficient HDL but weak reactivity with apoE-containing HDL in the first step, and the reaction intermediate (i.e., hydrogen peroxide derived from apoE-deficient HDL) is generated with the actions of cholesterol esterase and cholesterol oxidase. In the second step, subsequently, hydrogen peroxide immediately yields a quinone pigment in the presence of peroxidase, 4-aminoantipyrine, and the Trinder's reagent in the second reagent, and the absorbance of the reaction solution changes. Since such changes in absorbance are caused by the apoE-deficient HDL-C-based reaction, the extent of the changes in absorbance reflects the amount of apoE-deficient HDL-C. Such changes in absorbance are detected at an early stage of the second step. In contrast, apoE-containing HDL generates hydrogen peroxide through the action of a surfactant having reactivity with both apoE-containing HDL and apoE-deficient HDL or a surfactant having strong reactivity with apoE-containing HDL but weak reactivity with apoE-deficient HDL in the second reagent, cholesterol esterase, and cholesterol oxidase in the second step after hydrogen peroxide derived from apoE-deficient HDL is generated, which yields a quinone pigment in the presence of peroxidase, 4-aminoantipyrine, and Trinder's reagent. Such quinone pigment yield causes changes in absorbance of the reaction solution, and such changes in absorbance are caused by an apoE-containing HDL-C-based reaction. Thus, such changes in absorbance correspond to the amount of apoE-containing HDL-C. Hydrogen peroxide derived from apoE-containing HDL is assayed after hydrogen peroxide derived from apoE-deficient HDL is assayed. Accordingly, the overall changes in absorbance in the second step reflect the amount of both of apoE-deficient HDL-C and apoE-containing HDL-C. Specifically, the overall changes in absorbance in the second step reflect the amount of total HDL-C. Such changes in absorbance can be assayed with the use of an automatic analyzer, and multiple components, such as apoE-deficient HDL-C, apoE-containing HDL-C, and total HDL-C, can be simultaneously quantified with a single assay procedure by changing the conditions for analysis.

When the method of the present invention is carried out with the use of an automatic analyzer for which various assay conditions can be set, the assay conditions for multi-component analysis of the automatic analyzer are the conditions set for quantification of total HDL-C based on overall changes in absorbance in the second step. Other assay conditions include the conditions set for quantification of apoE-containing HDL-C based on the changes in absorbance between two points after the addition of the second reagent (i.e., after rapid changes in absorbance immediately following the addition of the second reagent and the final point of the reaction) in the second step.

The method for enzymatically quantifying cholesterol of the present invention is well-known in the art. As in the case of the first step, for example, cholesterol may be quantified by generating hydrogen peroxide from cholesterol ester and free cholesterol with the action of cholesterol esterase and cholesterol oxidase, and quantifying the hydrogen peroxide generated. Quantification of hydrogen peroxide may be carried out by, for example, allowing the hydrogen peroxide to react with a compound, which yields a quinone pigment upon such reaction, in the presence of peroxidase, and assaying the amount of the resulting quinone pigment by assaying absorbance or the like. A quinone pigment can be yielded using, for example, hydrogen peroxide, 4-aminoantipyrine, and a phenol-based or aniline-based hydrogen donor compound.

Among hydrogen donor compounds, examples of aniline-based hydrogen donor compounds include N-(2-hydroxy-3-sulfopropyl)-3,5-dimethoxyaniline (HDAOS), N-ethyl-N-sulfopropyl-3-methoxyaniline (ADP S), N-ethyl-N-sulfopropylaniline (ALPS), N-ethyl-N-sulfopropyl-3,5-dimethoxyaniline (DAPS), N-sulfopropyl-3,5-dimethoxyaniline (HDAPS), N-ethyl-N-sulfopropyl-3,5-dimethylaniline (MAPS), N-ethyl-N-sulfopropyl-3-methylaniline (TOPS), N-ethyl-N-(2-hydroxy-3-sulfopropyl)-3-methoxyaniline (ADOS), N-ethyl-N-(2-hydroxy-3-sulfopropyl)aniline (ALOS), N-ethyl-N-(2-hydroxy-3-sulfopropyl)-3,5-dimethoxyaniline (DAOS), N-ethyl-N-(2-hydroxy-3-sulfopropyl)-3,5-dimethylaniline (MAOS), N-ethyl-N-(2-hydroxy-3-sulfopropyl)-3-methylaniline (TOOS), and N-sulfopropylaniline (HALPS).

While the concentration of the compound that yields the quinone pigment is not particularly limited, the concentration of 4-aminoantipyrine, for example, is preferably 0.1 to 2.0 mM, and more preferably 0.5 to 1.5 mM, based on the total reaction mixture. The concentration of the phenol-based or aniline-based hydrogen donor compound is preferably 0.5 to 2.0 mmol/l. While the concentration of peroxidase is not particularly limited, it is preferably 0.4 to 5 U/ml, based on the total reaction mixture. Preferable reaction conditions (reaction temperature, reaction time, buffer, and pH) in the second step are the same as the preferable reaction conditions in the first step.

When the generated hydrogen peroxide is degraded with catalase in the first step, a catalase inhibitor, such as sodium azide, is used in the second step, so as to inhibit the catalase, because such inhibition is necessary in the second step.

EXAMPLES

The present invention is described in greater detail with reference to the examples. It should be noted that the present invention is not limited to the examples below. In the examples below, all "%" figures are by weight unless otherwise specified.

Reference Example 1

Fractionation of apoE-Containing HDL and apoE-Deficient HDL

The following procedure was carried out in order to recover apoE-containing HDL and apoE-deficient HDL fractions from the serum samples.

Potassium bromide (5.7687 g) was added to 18 ml of a serum sample obtained from a healthy volunteer to adjust the density (d) to 1.225, and the total lipoprotein was separated via ultracentrifugation at 65,000 rpm for 13 hours and 50 minutes. The resultant was subjected to dialysis with PBS (2 mmol/l, pH 7.4) and NaCl (30 mmol/l) for 24 hours, potassium bromide was removed, 2.0 ml of a 20% polyethylene glycol solution (average molecular weight: 6,000) was added to 2.0 ml of the test sample so as to coagulate lipoproteins other than HDL (e.g., CM, VLDL, and LDL), the coagulated fraction was trapped with a 0.25-μm filter, and HDL was then recovered. Thereafter, HDL was held on a heparin-fixed column, and HDL was divided into apoE-deficient HDL and apoE-containing HDL with the use of sodium chloride (30 to 200 mmol/l). The separated fraction was assayed in terms of total cholesterol, apoA1, and apoE. The results are shown in FIG. 1.

As shown in FIG. 1, HDL peaks appearing in the first half of the elution fraction contain apoA1, but apoE does not exist therein. That is, apoE-deficient HDL has been eluted. However, apoE peaks were observed in the second half of the peaks. Thus, HDL was divided into apoE-deficient HDL and apoE-containing HDL in the present example.

Example 1

Reactivity of Various Surfactants with apoE-Containing HDL and apoE-Deficient HDL In order to inspect the reactivity of various surfactants with apoE-containing HDL and apoE-deficient HDL subfractions, reagents having the compositions shown below were prepared. The second reagents were prepared using 100 types of surfactants.

| First reagents | |
|---|---|
| BES buffer (pH 7.0) | 100 mmol/l |
| HDAOS | 0.7 mmol/l |
| Cholesterol esterase | 0.8 U/ml |
| Cholesterol oxidase | 0.5 U/ml |
| Catalase | 80 U/ml |
| Magnesium chloride | 10 mmol/l |
| Second reagents | |
| BES buffer (pH 7.0) | 100 mmol/l |
| 4-Aminoantipyrine | 4.0 mmol/l |
| Peroxidase | 2.4 U/ml |
| Sodium azide | 0.1% |
| Surfactant of different type | 1.0% |

The first reagent (150 μl) was mixed with 2 μl of the test sample containing apoE-deficient HDL (fractions 25, 26, and 27) and apoE-containing HDL (fractions 44, 45, and 46) purified by the method of Reference Example 1, the resultant was allowed to react at 37° C. for 5 minutes (the first step), 50 µl of the second reagent was allowed to react therewith at 37° C. for 5 minutes, and the absorbance was assayed at 600 nm (primary wavelength) and 700 nm (secondary wavelength) (the second step). The amount of cholesterol was determined based on the assayed absorbance, and the determined value was compared with the amount of total cholesterol in the test sample to determine the reactivity with apoE-containing HDL and that with apoE-deficient HDL. In addition, the apoE-containing HDL response rate/apoE-deficient HDL response rate ratio was determined.

As shown in FIG. 2-1 to FIG. 2-4, the surfactants used were classified as follows based on the apoE-containing HDL response rate/apoE-deficient HDL response rate ratio: surfactants having an apoE-containing HDL response rate/apoE-deficient HDL response rate ratio of 0.7 to less than 1.3 that can be used to assay both subfractions; surfactants having an apoE-containing HDL response rate/apoE-deficient HDL response rate ratio of less than 0.7 that can be used to assay apoE-deficient HDL; and surfactants having an apoE-containing HDL response rate/apoE-deficient HDL response rate ratio of 1.3 or more that can be used to assay apoE-containing HDL. These surfactants may be adequately used to assay HDL subfractions of apoE-containing HDL and apoE-deficient HDL, or they may be used to assay all fractions.

In this example, fractions 25, 26, and 27 prepared in Reference Example 1 were selected as apoE-deficient HDL because substantially no apoE was found in these fractions, the amount of total cholesterol was large, and these fractions were thus considered to be adequate for determining reactivity. Fractions 44, 45, and 46 were selected as apoE-containing HDL because they had the largest amounts of apoE, and these fragments were thus considered to be adequate for determining reactivity. Similar results could be attained even when fractions with numbers close to the numbers mentioned above were selected.

Example 2

Quantification of Cholesterol in HDL

A reagent was prepared using Dispanol K-3 instead of the surfactant used for the second reagent in Example 1. Fractions containing VLDL, LDL, and HDL fractionated via HPLC were selected as test samples, 150 µl of the first reagent was mixed with 2 µl of the test sample, the resultant was allowed to react at 37° C. for 5 minutes, the second reagent (50 µl) was allowed to react at 37° C. for 5 minutes, and the absorbance was assayed at 600 nm (primary wavelength) and 700 nm (secondary absorbance). The amount of cholesterol was determined based on the absorbance assayed, and the determined value was compared with that in the test sample. The results of comparison are shown in FIG. 3.

Figure 3:
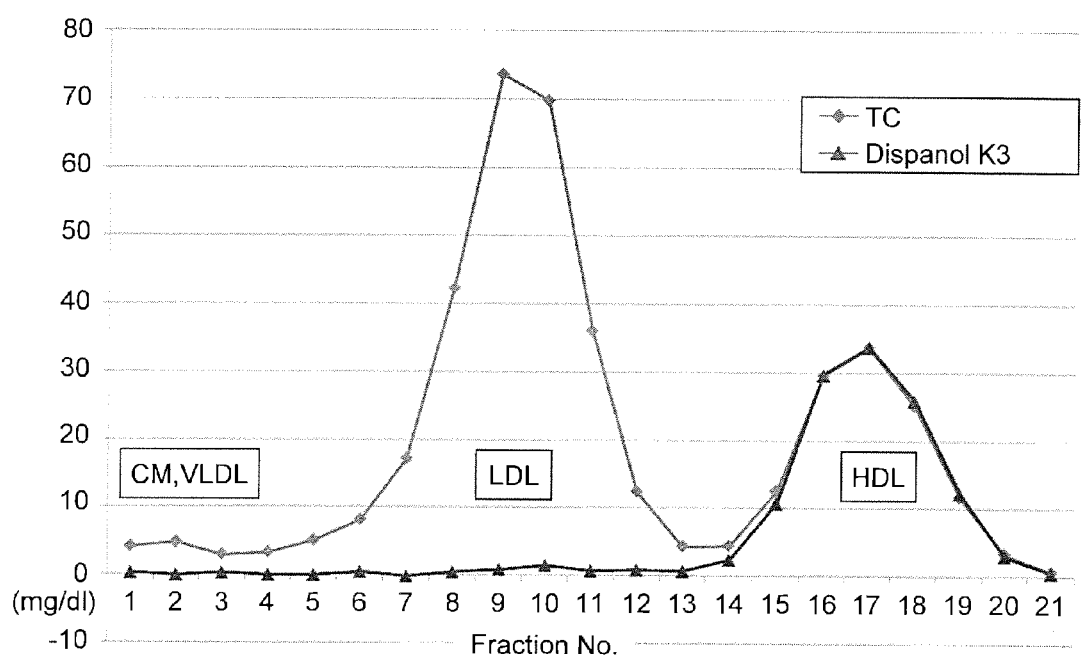

As shown in FIG. 3, a majority of the cholesterol in HDL can be quantified with the method described above, although no or substantially no cholesterol in other lipoproteins can be quantified. The method of the present invention allows selective quantification of cholesterol in HDL without the influence of other lipoproteins.

Example 3

Correlation with Other Method in Assay of apoE-Deficient HDL-C Concentration

A reagent was prepared using Adekatol LB-1220 instead of the surfactant used for the second reagent in Example 1.

The values obtained by conducting the PT-DS-Mg precipitation method as a control method for assaying apoE-deficient HDL were compared with the values obtained with the method of the present invention. The PT-DS-Mg precipitation method was carried out in the manner described below. A mixed solution of 3 g/l sodium phosphotungstate, 1.8 g/l dextran sulfate sodium, and 0.1 mol/l magnesium chloride (200 µl) was added and mixed with 200 µl of the test sample, and the resultant was then allowed to stand at room temperature for 10 minutes. Thereafter, the product was centrifuged at 2,000 g for 15 minutes, and 300 µl of the supernatant was recovered. The total cholesterol of the recovered fraction was assayed, and the concentration of apoE-deficient HDL-C was determined. Assay according to the method of the present invention was carried out in the same manner as in Example 1.

Figure 4:
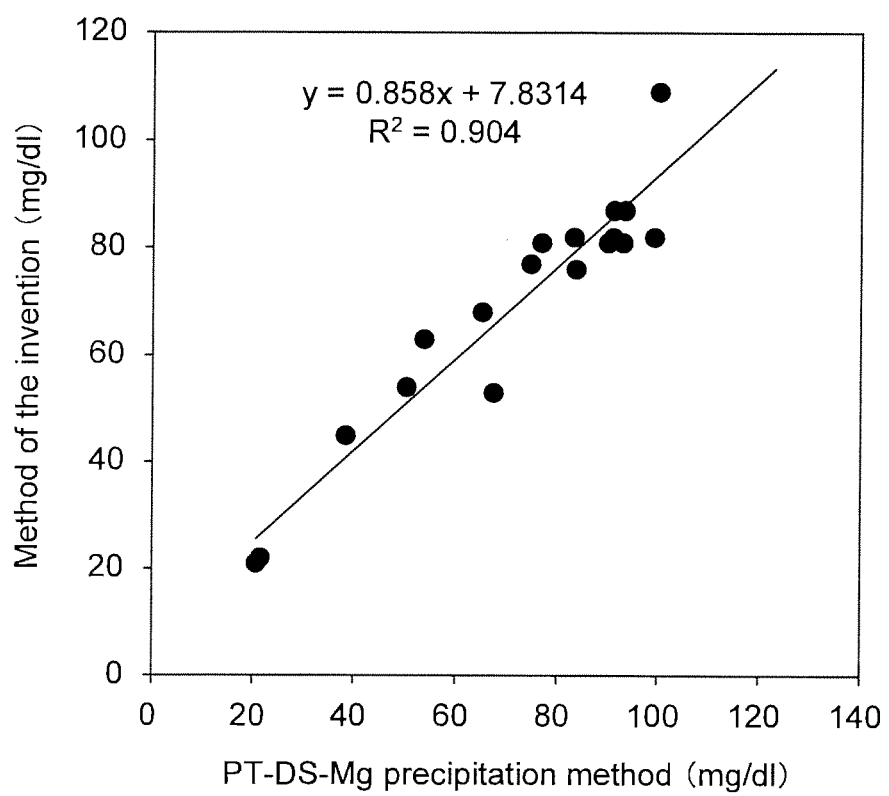

The correlation between the method of the present invention and the PT-DS-Mg precipitation method is shown in FIG. 4. As shown in FIG. 4, the results attained with the method of the present invention were good-correlated with the results attained with the PT-DS-Mg precipitation method as a method for apoE-deficient HDL assay (A Rapid and Simple Quantification of Human Apolipoprotein E-Rich High-Density Lipoproteins in Serum: Biochemical Medicine and Metabolic Biology, 47, 31-37, 1992).

Example 4

Correlation with Other Method in Assay of Concentration of apoE-Containing HDL-C and apoE-Deficient HDL-C A reagent was prepared using Adekatol LB-103 instead of the surfactant used for the second reagent in Example 1.

Figure 5:
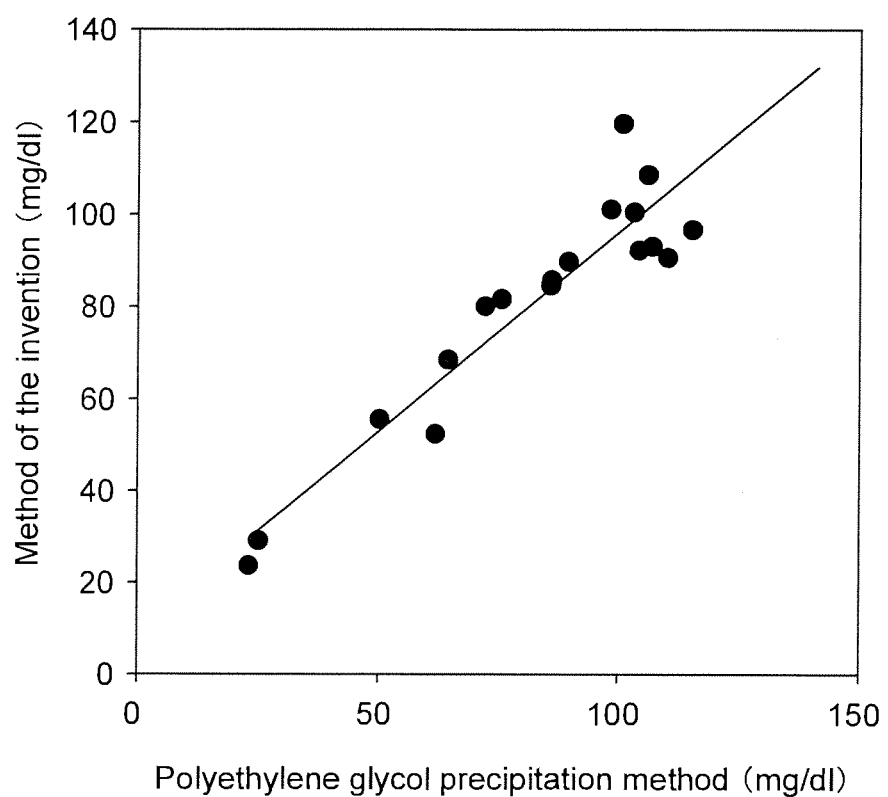
FIG. 5 shows the correlation between the method of Example 4 according to the present invention and the polyethylene glycol precipitation method.

The values obtained by conducting the polyethylene glycol precipitation method as a control method for assaying all HDL subfractions including apoE-containing HDL were compared with the values obtained with the method of the present invention. The polyethylene glycol precipitation method was carried out in the manner described below. A solution of 13% polyethylene glycol (200 µl; average molecular weight: 6,000) was added and mixed with 200 µl of the test sample, and the resultant was then allowed to stand at room temperature for 10 minutes. Thereafter, the product was centrifuged at 2,000 g for 15 minutes, and 300 µl of the supernatant was recovered. The total amount of cholesterol of the recovered fraction was assayed, and the concentration of the total of apoE-containing HDL-C and apoE-deficient HDL-C was determined. The method of the present invention was carried out in the same manner as in Example 1. The correlation between the method of the present invention and the polyethylene glycol precipitation method is shown in FIG. 5. As shown in FIG. 5, the results attained by the method of the present invention were good-correlated with the results attained by the polyethylene glycol precipitation method as a method for assaying all the HDL subfractions, including apoE-containing HDL.

All publications, patents, and patent applications cited herein are incorporated herein by reference in their entirety.

The invention claimed is:

1. A method of selectively and enzymatically quantifying cholesterol in apoE-deficient HDL by adding a surfactant having an apoE-containing HDL response rate/apoE-deficient HDL response rate ratio of less than 0.7 to a test sample, allowing cholesterol esterase and cholesterol oxidase to react therewith, and quantifying the hydrogen peroxide generated, wherein the surfactant having an apoE-containing HDL response rate/apoE-deficient HDL response rate ratio of less than 0.7 is selected from the group consisting of Polyoxyethylene nonylphenyl ether having an HLB of 16, Polyoxyethylene alkyl(coconut)amine having an HLB of 15.6, Polyoxyethylene stearylamine having an HLB of 15.4, Polyoxyethylene octyl phenyl ether having an HLB of 15, Polyoxyethylene stearylamine having an HLB of 12.8 and Polyoxyethylene beef tallow alkylamine having an HLB of 16.5.

2. A method of selectively and enzymatically quantifying cholesterol in apoE-containing HDL by adding a surfactant having an apoE-containing HDL response rate/apoE-deficient HDL response rate ratio of 1.3 or more to a test sample, allowing cholesterol esterase and cholesterol oxidase to react therewith, and quantifying the hydrogen peroxide generated, wherein the surfactant having an apoE-containing HDL response rate/apoE-deficient HDL response rate ratio of 1.3 or more is polyoxyethylene nonylphenyl ether having an HLB of 5 to 6.

3. A method of quantifying cholesterol in apoE-containing HDL comprising:
   (a) selectively and enzymatically quantifying cholesterol in apoE-deficient HDL by adding a surfactant having an apoE-containing HDL response rate/apoE-deficient HDL response rate ratio of less than 0.7 to a test sample, allowing cholesterol esterase and cholesterol oxidase to react therewith, and quantifying the hydrogen peroxide generated, wherein the surfactant having an apoE-containing HDL response rate/apoE-deficient HDL response rate ratio of less than 0.7 is selected from the group consisting of Polyoxyethylene nonylphenyl ether having an HLB of 16, Polyoxyethylene alkyl(coconut)amine having an HLB of 15.6, Polyoxyethylene stearylamine having an HLB of 15.4, Polyoxyethylene octyl phenyl ether having an HLB of 15, Polyoxyethylene stearylamine having an HLB of 12.8 and Polyoxyethylene beef tallow alkylamine having an HLB of 16.5;
   (b) enzymatically quantifying cholesterol in a total amount of HDL, including cholesterol in apoE-containing HDL, by adding a surfactant having an apoE-containing HDL response rate/apoE-deficient HDL response rate ratio of 0.7 to less than 1.3 to a test sample, allowing cholesterol esterase and cholesterol oxidase to react therewith, and quantifying the hydrogen peroxide generated, wherein the surfactant having an apoE-containing HDL response rate/apoE-deficient HDL response rate ratio of 0.7 to less than 1.3 is selected from the group consisting of 2-Ethylhexyl sulfate sodium salt, Polyoxyethylene alkyl ether having an HLB of 13.3, Polyoxyethylene laurylamine having an HLB of 6.2, Polyoxyethylene sorbitan monolaurate having an HLB of 16.7, Polyoxyethylene monooleate having an HLB of 13.7, Lauryl dimethyl aminoacetic acid betaine, Polyoxyethylene monolaurate having an HLB of 13.3, Polyoxyethylene sorbitan mono-coconut oil fatty acid ester having an HLB of 16.7, Polyoxyethylene alkyl ether having an HLB of 12, Polyoxyethylene monostearate having an HLB of 16.9, Polyoxyethylene alkyl ether having an HLB of 14, Polyoxyethylene sorbitan monostearate having an HLB of 14.9, Polyoxyethylene hydrogenated castor oil having an HLB of 12.5, Polyoxyethylene alkyl propylenediamine having an HLB of 6, and Sodium salt of lauryl sulfate; and
   (c) subtracting the value of cholesterol in apoE-deficient HDL determined by step (a) from the value of total cholesterol including cholesterol-containing HDL and apoE-containing HDL determined by step (b) to determine the cholesterol level in apoE-containing HDL, wherein step (a) and step (b) can be carried out in any order.

4. The method of quantifying cholesterol in HDL according to claim 1, which comprises a first step of erasing cholesterol in lipoproteins other than HDL in a test sample and a second step of quantifying cholesterol in HDL.

5. The method of quantifying cholesterol in HDL according to claim 2, which comprises a first step of erasing cholesterol in lipoproteins other than HDL in a test sample and a second step of quantifying cholesterol in HDL.

6. The method of quantifying cholesterol in HDL according to claim 3, which comprises a first step of erasing cholesterol in lipoproteins other than HDL in a test sample and a second step of quantifying cholesterol in HDL.

7. A method of quantifying cholesterol in apoE-containing HDL comprising: a first step of adding a surfactant having an apoE-containing HDL response rate/apoE-deficient HDL response rate ratio or less than 0.7 to a test sample, allowing the surfactant to selectively react with apoE-deficient HDL, and erasing or coagulating cholesterol in apoE-deficient HDL by way of the action of cholesterol esterase, cholesterol oxidase, and catalase; and a second step of adding a surfactant having an apoE-containing HDL response rate/apoE-deficient HDL response rate ratio of 0.7 to less than 1.3 or a surfactant having an apoE-containing HDL response rate/apoE-deficient HDL response rate ratio of 1.3 or more, and allowing the surfactant to react with remaining HDL in a test sample to quantify cholesterol in apoE-containing HDL, wherein:
   (a) the surfactant having an apoE-containing HDL response rate/apoE-deficient HDL response rate ratio of 0.7 to less than 1.3 is selected from the group consisting of 2-Ethylhexyl sulfate sodium salt, Polyoxyethylene alkyl ether having an HLB of 13.3, Lauryl alcohol alkoxylate, Polyoxyethylene laurylamine having an HLB of 6.2, Polyoxyethylene sorbitan monolaurate having an HLB of 16.7, Polyoxyethylene monooleate having an HLB of 13.7, Lauryl dimethyl aminoacetic acid betaine, Polyoxyethylene monolaurate having an HLB of 13.3, Polyoxyethylene sorbitan mono-coconut oil fatty acid ester having an HLB of 16.7, Polyoxyethylene alkyl ether having an HLB of 12, Polyoxyethylene monostearate having an HLB of 16.9, Polyoxyethylene alkyl ether having an HLB of 14, Polyoxyethylene sorbitan monostearate having an HLB of 14.9, Polyoxyethylene hydrogenated castor oil having an HLB of 12.5, Polyoxyethylene alkyl propylenediamine having an HLB of 6, and Sodium salt of lauryl sulfate; and
   (b) the surfactant having an apoE-containing HDL response rate/apoE-deficient HDL response rate ratio of 1.3 or more is polyoxyethylene nonylphenyl ether having an HLB of 5 to 6.

8. A method of simultaneously quantifying cholesterol in apoE-containing HDL and cholesterol in total amount of HDL comprising: a first step of adding a surfactant having an apoE-containing HDL response rate/apoE-deficient HDL response rate ratio of less than 0.7 to a test sample and generating hydrogen peroxide derived from cholesterol in apoE-deficient HDL; and a second step of detecting the hydrogen peroxide derived from cholesterol in apoE-deficient HDL at an early stage and simultaneously adding a surfactant having an apoE-containing HDL response rate/apoE-deficient HDL response rate ratio of 0.7 to less than 1.3 or a surfactant having an apoE-containing HDL response rate/apoE-deficient HDL response rate ratio of 1.3 or more and detecting the hydrogen peroxide derived from cholesterol in apoE-containing HDL, wherein:

(a) the surfactant having an apoE-containing HDL response rate/apoE-deficient HDL response rate ratio of 0.7 to less than 1.3 is selected from the group consisting of 2-Ethylhexyl sulfate sodium salt, Polyoxyethylene alkyl ether having an HLB of 13.3, Polyoxyethylene laurylamine having an HLB of 6.2, Polyoxyethylene sorbitan monolaurate having an HLB of 16.7, Polyoxyethylene monooleate having an HLB of 13.7, Lauryl dimethyl aminoacetic acid betaine, Polyoxyethylene monolaurate having an HLB of 13.3, Polyoxyethylene sorbitan mono-coconut oil fatty acid ester having an HLB of 16.7, Polyoxyethylene alkyl ether having an HLB of 12, Polyoxyethylene monostearate having an HLB of 16.9, Polyoxyethylene alkyl ether having an HLB of 14, Polyoxyethylene sorbitan monostearate having an HLB of 14.9, Polyoxyethylene hydrogenated castor oil having an HLB of 12.5, Polyoxyethylene alkyl propylenediamine having an HLB of 6, and Sodium salt of lauryl sulfate;

(b) the surfactant having an apoE-containing HDL response rate/apoE-deficient HDL response rate ratio of less than 0.7 is selected from the group consisting of Polyoxyethylene nonylphenyl ether having an HLB of 16, Polyoxyethylene alkyl(coconut)amine having an HLB of 15.6, Polyoxyethylene stearylamine having an HLB of 15.4, Polyoxyethylene octyl phenyl ether having an HLE of 15, Polyoxyethylene stearylamine having an HLB of 12.8 and Polyoxyethylene beef tallow alkylamine having an HLB of 16.5; and (c) the surfactant having an apoE-containing HDL response rate/apoE-deficient HDL response rate ratio of 1.3 or more is polyoxyethylene nonylphenyl ether having an HLB of 5 to 6.

* * * * *